United States Patent [19]

Wartman

[11] 4,240,415

[45] Dec. 23, 1980

[54] ORTHOPEDIC CAST

[75] Inventor: Lloyd H. Wartman, Norwalk, Conn.

[73] Assignee: WFR/Aquaplast Corp., Ramsey, N.J.

[21] Appl. No.: 970,626

[22] Filed: Dec. 18, 1978

Related U.S. Application Data

[63] Continuation of Ser. No. 772,090, Feb. 25, 1974, abandoned.

[51] Int. Cl.² ............................................. A61F 5/04
[52] U.S. Cl. ..................................... 128/90; 528/359
[58] Field of Search .................... 128/90; 260/901; 204/159.11; 528/359

[56] References Cited

U.S. PATENT DOCUMENTS

| | | | |
|---|---|---|---|
| 2,697,434 | 12/1954 | Rodman | 128/90 |
| 2,853,067 | 9/1958 | Puharich | 128/90 |
| 3,027,336 | 3/1962 | Gotz et al. | 128/90 |
| 3,111,469 | 11/1963 | Marans | 260/78.3 R |
| 3,259,607 | 7/1966 | Cherdron et al. | 528/359 |
| 3,373,741 | 3/1968 | Hill et al. | 128/90 |
| 3,442,265 | 5/1969 | Malven | 128/90 |
| 3,692,023 | 9/1972 | Phillips et al. | 128/90 |
| 3,763,858 | 10/1973 | Buese | 128/90 |
| 3,908,644 | 9/1975 | Neinart et al. | 128/90 |
| 4,019,505 | 4/1977 | Wartman | 128/90 |

Primary Examiner—C. Fred Rosenbaum
Attorney, Agent, or Firm—Norman S. Blodgett; Gerry A. Blodgett

[57] ABSTRACT

An orthopedic cast made of a thermoplastic polyester having a melting point between 50° C. and 100° C., particularly poly (epsilon-caprolactone) having a weight average molecular weight of over 5,000 subjected to electron radiation in the range from 0.25 to 15.0 megarads.

16 Claims, 4 Drawing Figures

ORTHOPEDIC CAST

This is a continuation of application Ser. No. 772,090 filed Feb. 25, 1974 and now abandoned.

BACKGROUND OF THE INVENTION

Plastic materials have been used successfully in the past to make formable splints and casts. Some of the plastics that have been used are polyisoprene (U.S. Pat. No. 3,490,444) and polychloroprene (U.S. Pat. No. 3,592,190). Copolymers of trioxane (U.S. Pat. No. 3,604,413) and several other thermoplastics have also been recommended. Recently, poly (epsilon-caprolactone) a crystalline polyester melting at 60° C., and its blends with poly-(vinyl alkyl ether) have been discovered to be excellent splint and cast materials (U.S. Pat. No. 3,692,023). Such a cost has been described in the patent application of Wartman Ser. No. 510,736 filed Oct. 20, 1975. All these polymers have low softening temperatures. In addition, they harden slowly when cooled from the melt to below their softening temperature. They can be heated to a temperature higher than their softening point, allowed to cool in room air temperature, and then molded to the patient without causing discomfort.

Examination of prior art materials based on these polymers in their molten form indicates that they possess another property desirable for easy forming to a smooth surface with good conformity and a lack of wrinkles, indentations or other defects imparted by the hand molding. The molten products do not flow excessively when unsupported by a back-up film, and internal gauze or some such structure. Distortion of the physical dimensions of a molten polymer can take place through viscous flow, elastic flow, or a combination of the two. Some of the prior art products, such as those based on polyisoprene or poly-chloroprene, distort in part by elastic flow. If a strip of molten polymer is manually extended and then released, it has some tendency to return to its original dimensions. However, viscous flow also takes place and permanent distortion beyond the original dimensions occurs. Consequently, when forming these materials, a permanent decrease in thickness can take place. If the therapist inadvertently stretches the material too much in forming it, the material becomes permanently elongated and unusable for the intended application. Also, reforming a splint, brace, or cast because of a loss of edema in the fitted body member is not possible because, while it is possible to enlarge the structure, reducing its dimensions is not feasible.

In order to provide as stable a structure as possible, so that excessive stretching does not occur in the molten state, the prior art materials generally contain sub-micron sized fillers such as fumed silica, asbestos, clay, or mica. These fillers exert a thixotropic effect and the viscosity, especially at low shear rates, is greatly increased.

This technique is also operable with poly (epsilon-caprolactone). However, considerable quantities of filler are required. About 10% of fumed silica is needed to achieve the required viscosity, while even larger quantities of clay or mica must be employed. Compounding these fillers into the plastic requires sophisticated, costly equipment. The density of the resulting plastic is higher and this is undesirable, because the splint or cast is heavier. Also, the presence of the filler causes the melt to be opaque, so that there is no visual indication that the material has reached the proper temperature for application.

The fillers which are most effective in achieving the thixotropic melt behavior are those with the smallest average particle size. These specialized products are quite expensive and, generally, they do not serve to reduce the cost of the end product. It would be advantageous to achieve the proper rheological properties in the melt using a cheap, larger particle size filler such as calcium carbonate. Heretofore, this has not been feasible because the amounts necessary to attain the proper level of thixotropy are too great and result in a deterioration of the physical properties of the product.

With these and other objects in view, as will be apparent to those skilled in the art, the invention resides in the combination of parts set forth in the specification and covered by the claims appended hereto.

It is, therefore, an outstanding object of this invention to provide an orthopedic cast, splint, or brace which is clean and simple to apply.

Another object of this invention is to provide an orthopedic cast material which is self-indicating, i.e., is transparent when ready to apply and opaque when non-formable.

A further object of this invention is to provide an orthopedic cast, which is elastic in the molten state and can be reformed to its pre-application shape by remelting and allowing to relax to its original geometry.

Another object of this invention is to provide a cast which has molding characteristics which are relatively insensitive to the temperature of heating and application.

Another object of this invention is to provide a cast which conforms readily to the irregular shapes of the body member to be fitted.

Another object of this invention is the provision of an orthopedic cast which can be applied in a short time.

A further object of the present invention is the provision of an orthopedic cast which is light, strong, and sanitary in use, which allows circulation of air under the cast, and which permits washing of the limb.

It is another object of the instant invention to provide an orthopedic cast which does not require cumbersome equipment to apply.

A still further object of the invention is the provision of an orthopedic cast which reliably adhers to itself during application.

It is a further object of the invention to provide an orthopedic cast which can be applied to the patient while the cast is still in a plastic state.

It is a still further object of the present invention to provide an orthopedic cast which can be pre-formed and which will maintain the pre-formed shape even when rendered plastic.

With these and other objects in view, as will be apparent to those skilled in the art, the invention resides in the combination of parts set forth in the specification and covered by the claims appended hereto.

SUMMARY OF THE INVENTION

This invention involves an orthopedic cast system in which a cast is formed by wrapping a sheet of theremoplastic polyester which has been brought to its melting point of 50° C. to 100° C. around the subject limb and allowing the sheet to cool to hardness. The sheet is preferably heated in water and bonds to itself while molten. The preferred polyester is poly (epsilon-caprolactone) having a weight-average molecular weight of over 5,000, subjected to electron radiation in the range from 0.25 to 15.0 megarads and having a half-time crystallization at 36° C. of 0.5 to 10.0 minutes.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
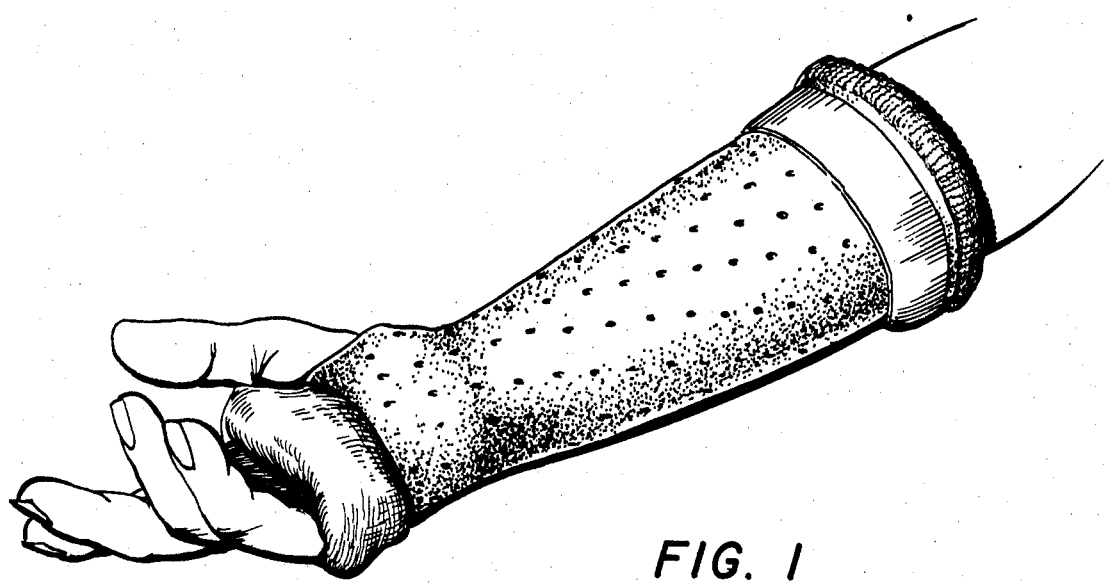
FIG. 1 is a perspective view of a wrist cast embodying the principles of the present invention in use on a human limb.

Referring to the drawings, in FIG. 1 an orthopedic cast 10 is shown in use on the arm of a human being.

Figure 2:
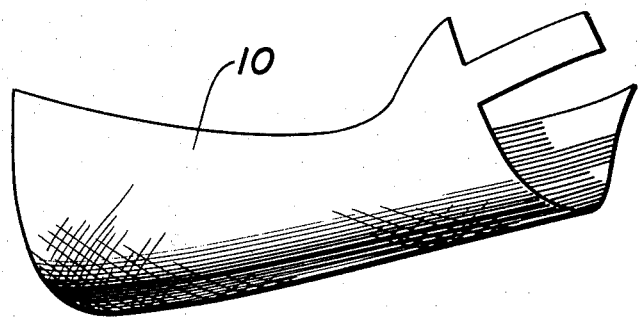
FIG. 2 is a perspective view of a pre-formed cast ready for heating and application.

FIG. 2 shows the cast 10 in a pre-formed condition, ready for application to a human limb.

Figure 3:
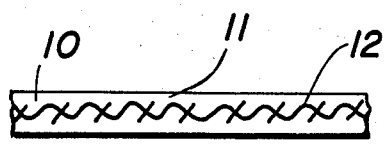
FIG. 3 is a cross-sectional view of a continuous composite sheet.

In FIG. 3, a cross-section of the cast is shown with a polyester 11 applied to a substrate 12 to provide a closed cast.

Figure 4:
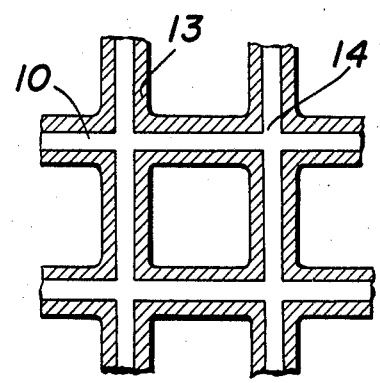
FIG. 4 is a cross-sectional view of a foraminous, composite sheet.

FIG. 4 shows a sectional view of the cast 10 with a polyester applied in the form of a coating 13 applied to an open network substrate 14 to provide a foraminous cast.

The orthopedic cast is formed by wrapping a sheet of thermoplastic polyester which has been brought to its melting point of 50° C. to 100° C. around the subject limb and allowing the sheet to cool to hardness. The sheet is preferably heated in water and bonds to itself while molten. The preferred polyester is poly (epsilon-caprolactone) having a weight-averaged molecular weight of over 5,000, which has been subjected to electron radiation in the range from 0.25 to 15.0 megarads, so that it's half-time crystallization is in the range from 0.5 to 10.0 minutes. The cast, formed of a linear polyester poly (epsilon-caprolactone) in the form of sheets, is irradiated. At a 15 megarad dose, a continuous internal network is formed, as indicated by the elastic behavior of the molten polymer.

The following are examples of the operation of the invention:

EXAMPLE I

Three sheets of poly (epsilon-caprolactone) with dimentions of 36"×18" 1/16" were subjected to electron radiation to total dosages of 5, 10, and 15 megarads. The dosage per pass was 2½ megarads. Multiples of this dosage were achieved by repeated passage of the sheets under the radiation source. Pieces ½"×4"×1/16" were cut from the sheets and melted in a water bath at 70° C. When held by one end, the 5 megarad sample flowed until the floor was reached, the 10 megarad sample distorted somewhat but became immobile by crystallizing before it reached the floor. The 15 megarad sample did not flow. It could be manually distorted but it returned to its original shape on release. A ½"×4"×1/16" piece of the 15 megarad sample was melted as previously described. The molten material was stretched along its 4" axis to its elastic limit (about 20") and held there until immobilized by crystallization due to cooling. The stretched piece was replaced in hot water. It immediately relaxed to its original ½"×4"×1/16" dimensions. A 2"×2"×1/16" piece was melted, firmly gripped on its edges, and then forced down over the extended index finger of a subject, where it was allowed to cool. The stretched piece accurately reproduced all features of the finger including the nail, knuckle etc. On removal and replacing in hot water, it resumed its original dimensions.

EXAMPLE II

Sheets of poly (epsilon-caprolactone) ⅛" and 1/16" thick were subjected to a total dosage of 15 megarads. This time the dose rate was 5 megarads per pass. The dose rate has an effect on the course of the reaction, as shown by the fact that, after 15 megarads, internal gassing was observed in the samples. Also, the cross-linking reaction was enhanced, as shown by the fact that the modulus of elasticity of the melt was much higher than observed in the samples given a dosage of 15 megarads, but at a rate of 2½ megarads per pass.

EXAMPLE III

Sheets of poly (epsilon-caprolactone) ⅛" thick were subjected to electron irradiation at a dose rate of 2½ megarads per pass for a total of 12½ megarads. Several types of splints and braces were made from sections of the sheets by people skilled in the art of using the prior art splint materials, such as those based on trans polyisoprene. In their opinion, the product based on electron treated poly (epsilon-caprolactone) had several advantages, such as improved moldability, over the prior art products. Also, the fact that the poly (epsilon-caprolactone) becomes transparent when molten is an advantage, because it allows better positioning of the splint in relation to body structure.

EXAMPLE IV

Molded plaques 12"×12"×⅛" were prepared from a mixture of 95% poly (epsilon-caprolactone) and 5% trimethylolpropane trimethacrylate. The mixture was prepared by conventional extrusion compounding methods. Some of the plaques were subjected to a single pass of 3 megarads, while others were given two passes of 3 megarads each. The molten products were very tightly cross-linked, as shown by a high modulus of elasticity in the melt.

It should be noted that it is quite surprising that this polyester is so readily cross-linked by electron radiation. The two reactions of importance in determining whether a given polymer forms a network structure or degrades under the influence of radiation are the chain scission reaction and the cross-linking reaction. It has been shown (on a theoretical basis) that when the rate of the chain scission reaction is four times or more times the rate of the cross-linking reaction, the formation of a continuous cross-linked network in the polymer is not possible. The general rule whereby one may predict from the chemical structure of a polymer if it will degrade or cross-link is described by Miller et al in the Journal of Polymer Science Volume 14, page 503. As quoted by Hoffman at the Eastern New England Society of Plastics Engineers Regional Technical Conference on Mar. 21, 1975, "—if a carbon atom in the polymer has two hydrogens substituted, chain degradation prevails." One of the carbon atoms in the repeating structure of poly (epsilon-caprolactone) has two hydrogens substituted by an oxygen. Clearly, poly (epsilon-caprolactone) does not behave as would be predicted by Miller.

The effect of electron radiation on another polyester, poly (ethylene-terephthalate), the condensation polymer of ethylene glycol and terephthalic acid, has been determined. Under the influence of electron radiation this polymer can be cross-linked. However, the dosages required are extremely high and impractical for commercial use. In the experiments of Hellwege et al (Kolloid Zeitschrift 188, 11) 2,000 megarads were required to form a gel fraction of 12% while 4,000 megarads were needed to yield a gel fraction of 30%. The remainder of the polymer remains soluble and is not connected to the network gelled polymer by primary valence bonds. In contrast, 15 megarads are more than sufficient to cross-link poly (epsilon-caprolactone).

It is known that certain other polyesters can be cross-linked by ionizing radiation. However, these are unsaturated polyesters in which the difunctional acid contains a double bond (e.g. derived from maleic, itaconic acid, etc.). In such case, the mechanism of the cross-linking reaction is quite different, because polymerization takes place through the double bond structure. The ionizing radiation initiates the polymerization by first forming free radicals which then react with the double bonds in much the same manner as with the polymerization of a vinyl monomer.

The effects of radiation cross-linking on the properties of the molten polymer of the invention are quite remarkable. This can be demonstrated on strips of the plastic, $\frac{1}{2}'' \times 4'' \times 1/16\ ''$. These are placed in water at 70° C. until molten after they are suspended from one end. The control sample, not irradiated, flows under its own weight until the lower end reaches the floor. At low dosages (around 5 megarads) the flow still occurs but perceptibly slower. Higher dosages are sufficient to eliminate flow. At around 15 megarads the melt is elastic. If distorted manually and then released, it returns to its original dimensions. The stiffness of the elastic melt or, more properly, its modulus of elasticity can also be varied. A highly cross-linked sample made by using high dosages distorts less at a given stress level than one made at lower radiation levels.

The radiation dosage required to effect cross-linking can be markedly reduced, if certain additives are incorporated into the poly (epsilon-caprolactone). The effective additives are chemicals containing two or more double bonds in each molecule. The presence of the trimethacrylate of trimethylolpropane at a concentration of two percent in poly (epsilon-caprolactone) reduces the dosage of irradiation required to cross-link the polymer by at least a factor of four. Other polyunsaturated molecules, such as the polyfunctional acrylates and methacrylates of polyols, neoprene and butadiene rubbers are also useful to promote the cross-linking reaction.

It is clear that inexpensive fillers can be employed along with electron irradiation or other means of cross-linking to achieve a lower cost product. The advantage of the transparency of the molten material might be lost. It is readily apparent that, by use of cross-linking, the rheological characteristics of poly (epsilon-caprolactone) in its molten form can be modified as desired to suit the needs of the application to be considered. For general use in fabricating splints and similar structures a product with some elasticity is desired. It can be readily stretched over the member to be fitted and held in place until it becomes immobile by crystallization. If per chance, the initial fitting is not suitable, the deformed piece can be brought back to its original shape by simply replacing it in hot water. It is then ready for reuse.

In applying the cross-linked poly (epsilon-caprolactone) to the body member to be immobilized should be noted that excellent conformity to the shape of the body member without pressure points, etc., is readily achieved. The elasticity of the melt allows easy stretching over protuberances and close fit to adjacent areas. In general, it is easier to achieve good conformity to body members with the elastic melt than it is with any of the prior art materials used for this purpose.

The unfilled, cross-linked material has another obvious advantage over the filled materials of the prior art, that is, it becomes transparent when the polymeric crystals are melted and the material is ready for molding to the patient. The therapist can observe the change visually without need for careful control of the temperature or time of heating. The therapist or physician can direct his attention to other needs of the patient, while the splint or cast is being heated. The clarity of the melt also facilitates application to the patient, because it is easy to observe the exact positioning of the structure in relation to the body member.

Another advantage of the elasticized material is that it is less sensitive to temperature in the molten form than the prior art materials. As is well known, elastic distortion is a much lower activation energy process than viscous flow. Viscosity decreases rapidly with increasing temperature, whereas the elastic modulus decreases only moderately with increasing temperature. Hence, the temperature to which the elastic material is heated is not narrowly critical. Also, it is not necessary to achieve a uniform temperature in the melt. This allows one to use less sophisticated heated equipment. For example, it has been noted that the water in an unstirred electric frying pan tends to be hottest directly above the heating element. No adverse effect of the non-uniform temperature is noted with the cross-linked poly (epsilon-caprolactone). On the other hand, difficulties with this type of equipment are found with the prior art materials.

Another unexpected advantage of the cross-linked material can also be observed: uncross-linked polycaprolactone in its molten form tends to stick to nearly everything with which it comes in contact. To obviate this problem, it is advisable to use a light coating of petrolatum or some similar material on the hands and on the tray in which it is heated. The electron radiated material has much less tendency to stick and coatings of that type are not needed. Despite the presence of cross-links in the polymer, the rate of hardening from the melt is only slightly greater than for the uncross-linked material. Hence, times required for application are only slightly affected, if at all.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. An orthopedic cast comprised of poly (epsilon-caprolactone) having a formula

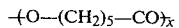

where x makes the weight average molecular weight greater than 5,000 subjected to electron radiation in the range from 0.5 to 15.0 megarads and having a melting point in the range from 50° C. to 100° C. with a half-time crystallization at 36° C. of between 0.5 minute and 10.0 minutes.

2. An orthopedic cast as recited in claim 1, wherein the poly (epsilon-caprolactone) is in the form of a precast element.

3. An orthopedic cast as recited in claim 1, wherein the poly (epsilon-caprolactone) is coated on a substrate, the substrate being a solid at the melting point of the poly (epsilon-caprolactone).

4. An orthopedic cast as recited in claim 1, wherein the substrate is a netting and the polyester is coated around each strand of the netting to form a foraminous sheet.

5. A method of forming an orthopedic cast comprising the steps of:
 (a) forming a preform sheet of poly (epsilon-caprolactone) of weight average molecular weight greater than 5,000 having a melting point of between 50° C. and 100° C.,
 (b) subjecting the sheet to electron radiation in the range from 5.0 to 15.0 megarads,
 (c) heating the sheet to its softening point,
 (d) forming the sheet into a desired shape, and
 (e) allowing the sheet to cool below its melting point.

6. A method as recited in claim 5, wherein the sheet is heated by immersing it in water at a suitable temperature.

7. A method as recited in claim 5, wherein the sheet contains a mixture of 95% poly (epsilon-caprolactone) and 5% trimethylolpropane trimethacrylate.

8. A method of forming an orthopedic cast comprising the steps of:
 (a) forming a preform sheet of poly (epsilon-caprolactone) of weight average molecular weight greater than 5,000 having a melting point of between 50° C. and 100° C.,
 (b) subjecting the sheet to electron radiation in the range from 0.25 to 15.0 megarads,
 (c) heating the sheet to its softening point,
 (d) forming the sheet into a desired shape, and
 (e) allowing the sheet to cool below its melting point.

9. A method as recited in claim 8, wherein the sheet is heated by immersing it in water at a suitable temperature.

10. A method as recited in claim 8, wherein the sheet contains a mixture of 95% poly (epsilon-caprolactone) and 5% trimethylolpropane trimethacrylate.

11. A method of forming an orthopedic cast comprising the steps of:
 (a) forming a preform sheet of poly (epsilon-caprolactone) of weight average molecular weight greater than 5,000 having a melting point of between 50° C. and 100° C. mixed with a radiation-sensitive cross-linking agent,
 (b) subjecting the sheet to electron radiation in the range from 3.0 to 15.0 megarads,
 (c) heating the sheet to its softening point,
 (d) forming the sheet into a desired shape, and
 (e) allowing the sheet to cool below its melting point.

12. A method as recited in claim 11, wherein the sheet is heated by immersing it in water at a suitable temperature.

13. A method as recited in claim 11, wherein the sheet contains a mixture of 95% poly (epsilon-caprolactone) and 5% trimethylolpropane trimethacrylate.

14. A method of forming an orthopedic cast comprising the steps of:
 (a) forming a preform sheet of poly (epsilon-caprolactone) of weight average molecular weight greater than 5,000 having a melting point of between 50° C. and 100° C. mixed with a radiation-sensitive cross-linking agent,
 (b) subjecting the sheet to electron radiation in the range from 0.25 to 15.0 megarads,
 (c) heating the sheet to its softening point,
 (d) forming the sheet into a desired shape, and
 (e) allowing the sheet to cool below its melting point.

15. A method as recited in claim 14, wherein the sheet is heated by immersing it in water at a suitable temperature.

16. A method as recited in claim 14, wherein the sheet contains a mixture of 95% poly (epsilon-caprolactone) and 5% trimethylolpropane trimethacrylate.

* * * * *